United States Patent
Doerr et al.

(10) Patent No.: US 8,583,210 B2
(45) Date of Patent: Nov. 12, 2013

(54) APPARATUS AND METHOD FOR COMMUNICATION BETWEEN MRI SYSTEM AND IMPLANTABLE MEDICAL DEVICES

(75) Inventors: Thomas Doerr, Berlin (DE); Ingo Weiss, Berlin (DE)

(73) Assignee: BIOTRONIK CRM Patent AG, Baar (CH)

( * ) Notice: Subject to any disclaimer, the term of this patent is extended or adjusted under 35 U.S.C. 154(b) by 405 days.

(21) Appl. No.: 12/972,452

(22) Filed: Dec. 18, 2010

(65) Prior Publication Data
US 2011/0152673 A1    Jun. 23, 2011

Related U.S. Application Data

(60) Provisional application No. 61/288,859, filed on Dec. 22, 2009.

(51) Int. Cl.
*A61B 5/05*    (2006.01)
(52) U.S. Cl.
USPC ............................. 600/411; 607/60; 607/63

(58) Field of Classification Search
USPC ............ 600/410, 411; 607/27, 30, 31, 32, 60, 607/63
See application file for complete search history.

(56) References Cited

U.S. PATENT DOCUMENTS

| | | |
|---|---|---|
| 2005/0070787 A1 | 3/2005 | Zeijlemaker |
| 2005/0070975 A1 | 3/2005 | Zeijlemaker et al. |
| 2009/0138058 A1 | 5/2009 | Cooke et al. |

FOREIGN PATENT DOCUMENTS

| | | |
|---|---|---|
| EP | 2062525 A2 | 5/2009 |
| WO | 2006/124481 A2 | 11/2006 |
| WO | 2007/124273 A1 | 11/2007 |

OTHER PUBLICATIONS

European Search Report dated Dec. 29, 2011, 8 pages.

*Primary Examiner* — Parikha Mehta
(74) *Attorney, Agent, or Firm* — ARC IP Law, PC; Joseph J. Mayo

(57) ABSTRACT

A device and a method for handling and withstanding electromagnetic fields, specifically such fields as occur in magnetic resonance tomography examinations (i.e., MRT or MRI). This refers in particular to an IMD that can transmit data and/or parameters to an MRT device.

15 Claims, 4 Drawing Sheets

APPARATUS AND METHOD FOR COMMUNICATION BETWEEN MRI SYSTEM AND IMPLANTABLE MEDICAL DEVICES

This application claims the benefit of U.S. Provisional Patent Application 61/288,859, filed on Dec. 22, 2009, which is hereby incorporated by reference in its entirety.

BACKGROUND OF THE INVENTION

1. Field of the Invention

Embodiments of the invention relate to a device and a method for handling electromagnetic fields, specifically, such fields as occur in devices for magnetic resonance tomography. ("MRT" or "MRI" stand for magnetic resonance tomography and magnetic resonance imaging respectively, wherein these two acronyms are used interchangeably herein).

2. Description of the Related Art

Although MRI examinations are becoming increasingly important in diagnostic medicine, a certain fraction of patients is contraindicated for MRI examinations. This type of contraindication can be caused by an at least partially implanted medical device (hereafter also: implant or IMD).

In order to be able to effect MRI examinations despite this fact, various approaches are known that relate either to the implementation of the MRI examination or to the implantable medical device.

US 2005/0070787 A1 thus discloses an approach whereby communication is established between an MRI device and an implant, thereby enabling the implant with information from the MRI device to deactivate one or more components of the implant during the delivery of RF pulses by the MRI device. To this end, as is described, it is necessary for communication to take place between implant and MRI device, which action requires a common communications protocol and compatible communications capabilities on each side. Aside from the thus necessary compatibility requirements and additionally necessary communications units, specifically on the side of the MRI devices, a further disadvantage is the long transitional period involved until a significant fraction of the MRI devices allow for safe MRI examinations of implant patients to occur.

A similar approach is pursued by EP 2 062 525. This describes an RFID system on electrode leads belonging to an implant that allows for a flow of information from the RFID tag to an MRI device. This system thus requires MRI devices that have a unit to read the RFID tags. Aside from the thus necessary compatibility requirements and additionally necessary RFID units, specifically on the side of the MRI devices, a further disadvantage is the long transitional period involved until a significant fraction of the MRI devices allow for safe MRI examinations of implant patients to occur through existing RFID read units.

In addition, both prior-art systems require the given MRI device to be equipped with updated information about the specific implant.

BRIEF SUMMARY OF THE INVENTION

It is therefore the object of embodiments of the invention to eliminate the disadvantages of the prior art and to provide an implantable medical device that allows for a safe examination using MRI methods. The problem is solved by an implantable medical device (IMD) having the features as claimed herein.

An IMD comprising an information memory, a communications unit, connectable to at least one antenna and/or at least one telemetry antenna, a control unit, and a unit to detect electromagnetic interference fields, wherein the previously-listed individual features of the IMD are connectable either directly or indirectly to at least the communications unit and the control unit, and at least the control unit is connectable directly to the communications unit, wherein the control unit receives a first signal from the unit for detecting electromagnetic interference fields whenever an electromagnetic interference field is detected and/or the control unit receives a second signal transmitted by an MRI device through the communications unit and the control unit causes the communications unit to emit a third signal through the at least one antenna and/or the at least one telemetry antenna, which signal is interpretable by the MRI device, wherein the control unit can cause the emission of the third signal both directly after receiving the first and/or the second signal, or time-delayed after receiving the first and/or the second signal.

What is understood by the designation "interpretable" is that the MRI device can process said third signal either directly by a communications unit, and/or that the MRI device receives said third signal during the MRI test and incorporates it into the image formation and thus information unit contained in said third signal is transmitted from the IMD to the display screen of the MRI device, and/or said third signal interferes with the signal processing of the MRI device in such a way that the test is halted. What is understood here by signal are not only single pulses or individual pulse sequences but also more complex signals and/or signal sequences and/or repetitions of signal sequences and/or variations of signals and/or of more complex signals and/or of signal sequences and/or repetitions of signal sequences.

One or more embodiments of the invention enable an implant to send the information required for patient safety to a magnetic resonance device which then adjusts automatically to the respective implant safety specifications, and/or to alert the user at the display screen about the implant and/or the requisite settings for safe use. Beyond the timing of the sequences, however, the information can also contain data on the maximum allowed power, maximum scan time, and do this in turn as a function of the patient position in the scanner. The power restriction here is transmitted both for the RF system as well as the gradient system, and is generally a function of the static magnetic field strength.

The transmission of the information—in the simplest case even just the signaling of its presence by generating an intended image interference—can be effected here at the initiative of the implant. Another solution according to the invention provides that this information be requested at the initiative of the magnetic resonance device, and specifically implemented as passive RFID (radio frequency identification).

What is preferred is that the information memory contain data and/or parameters that provide a risk-free MRI examination or an MRI examination with reduced risks, wherein these data and/or parameters are transmitted to the MRI device from the communications unit with the third signal using the at least one antenna and/or the at least one telemetry antenna and/or other wireless transmission method whenever an electromagnetic interference field has been detected and/or the communications unit has detected a connection to the MRI device. Data in this context relate to the data of the IMD, while the parameters relate to technical or physiological parameters of the MRI examination. Physiological parameters would be, by way of example, the position of the patient, the permitted examination regions, position of the implant and/or of implant components such as electrodes. In principle, both types of information are suitable for ensuring a safe MRI examination, although in particular the transmission of parameters is preferred.

What is also preferred is that the information memory for safety-relevant information be a nonvolatile memory.

What is furthermore preferred is that the detection of the electromagnetic interference be linked to exceeding an adjustable threshold value.

What is also preferred is that the unit for detecting electromagnetic interference fields transmit the measured values to the control unit, and that the control unit adjust the information and/or parameters according to the measured values before these are transmitted from the communications unit to the MRI, wherein this adjustment is based on values and/or algorithms that are stored in the information memory.

What is similarly preferred is that the third signal comprise at least one of the following values and/or parameters: maximum allowable RF power, maximum allowable gradient performance, maximum allowable scan duration, possibly as a function of one more of the other parameters, patient position, maximum allowable examination time, and/or parameters for synchronizing MRI scans and/or MRI read-out phases, and IMD activity relative to signal detection and/or delivery of therapy.

What is also preferred is that the signaling to the MRI device be effected through a targeted generation of image interference with said third signal.

What is preferred in particular is that in the read-out phase of the MRI scanner the IMD emit a signal to effect image interference on an appropriate Larmor frequency, wherein the signal to effect image interference has a predeterminable modulated amplitude.

What also preferred in particular is that the Larmor frequency be determined from a measurement of a static magnetic field and/or of the frequency of the previous electromagnetic interference by means of a unit for detecting electromagnetic interference fields.

What is also preferred in particular is that the configuration in terms of the carrier frequency and/or the modulation type and/or the modulation frequency and/or the modulation depth of the signal initiated by the communications unit, which signal effects image interference, is computed from the measurements of the unit for detecting electromagnetic interference fields.

What is also preferred is that an adjustment of the measurement parameters of the MRI device to the IMD be performed automatically and/or manually, wherein the adjustment of one of the measurement parameter can also result in a denial of an MRI examination.

What is furthermore preferred is that the maximum allowable performance values for the MRI device, which values are transmitted to the MRI device, are adjustable by the control unit based on the updated measurement values of the unit for detecting electromagnetic interference fields.

What is also preferred is that the IMD not have an internal power supply or that such a power supply not be available due to the detection of an electromagnetic interference and/or that the use of any battery present to provide communication with the MRI device be dispensed with so as to remove the load from the battery, wherein said third signal is transmitted by the communications unit by an approach whereby the power induced by the MRI device is used to cover the power requirement of the communications unit for transmitting said third signal to the MRI device.

What is similarly preferred is that the antenna or antennas for communicating with an MRI device be composed of elongated subsystems, such as but not limited to, for example, electrodes of cardiac pacemakers, defibrillators/cardioverters, devices to effect cardiac resynchronization, or neurostimulators, and/or an already-integrated antenna for RF communication.

What is also preferred is that the communication between MRI device and IMD be bidirectional, or the communication between MRI device and IMD be bidirectional and that the MRI device, after receiving the parameters that have been transmitted by the communications unit of the IMD, transmit an acknowledgement to the IMD, after which the IMD ceases to transmit said third signal, or at least modifies the amplitude and/or other parameters of said third signal.

What is similarly preferred is that at least one additional action out of the following actions be initiated when electromagnetic interference fields are detected: switching to an MRI-safe state, remaining for an extended time in an MRI-safe state or state that is insensitive to electromagnetic interference fields, and the delivery of a therapy and/or detection of electrical states in the tissue is permitted only within time windows in which no electromagnetic interference fields are detected, and/or that a reconstruction of a measurement is implemented for those regions in which detection is not permitted due to electromagnetic interference fields having been detected.

What is furthermore preferred is that the unit for detecting electromagnetic interference fields include at least one of the following sensors or indicators: GMR sensor, MagFET sensor, Hall sensor, electrooptical converter as an indicator, the monitoring of battery voltages during capacitor charging processes as an indicator, the detection of RF fields as an indicator, the detection of magnetic gradient fields as an indicator, the detection of currents induced by electromagnetic fields as an indicator, the detection of specific vibrations, or components designed as sensors to detect vibrations induced by Lorentz forces as an indicator. What is meant by indicators here are methods and/or devices that provide indications about the presence of electromagnetic interference fields.

What is preferred in particular is that in addition to at least one of the above-referenced sensors or indicators a position sensor or self-calibrating position sensor be present. This or these position sensors by determining the posture or the position of the patient provide an additional indicator as to whether the patient is located in an MRI device or other electromagnetic interference sources are present.

In addition to the devices referenced above, certain methods are also relevant relating to the use of an IMD within the range of action of an MRI device, which methods utilize an IMD according to one of the foregoing claims.

BRIEF DESCRIPTION OF THE DRAWINGS

Certain aspects of the invention are illustrated in FIG. 1-4.

DETAILED DESCRIPTION OF THE INVENTION

Figure 1:
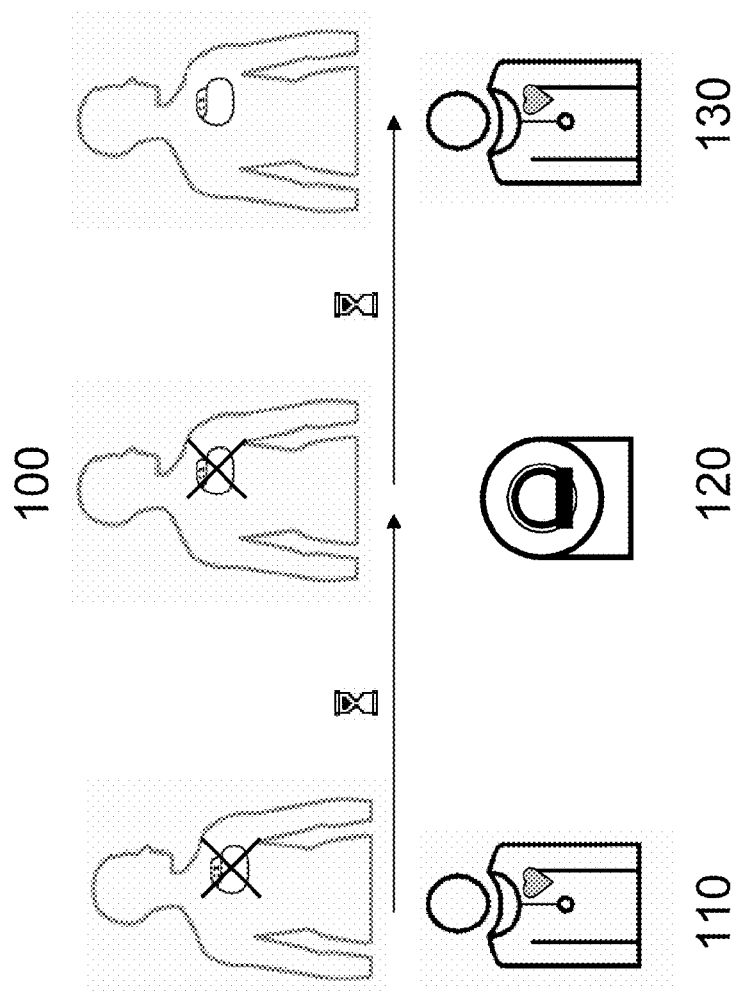
FIG. 1 is a schematic view illustrating the sequence of an MRI examination.

FIG. 1 describes the prior art in which the ICD patient 100 undergoes aftercare by a cardiologist before the scheduled MRT examination and the ICD is turned off 110. The MRT examination by a radiologist 120 takes place with a time delay counted in hours up to days. After a further delay, the patient is again treated by the cardiologist 130 and the ICD is once again turned on. During this entire period from 110 to 130, the patient is without the protection of the implanted defibrillator and essentially without rhythm monitoring. Currently this remaining risk is accepted as measured against the benefit of the MRT examination.

Figure 2:
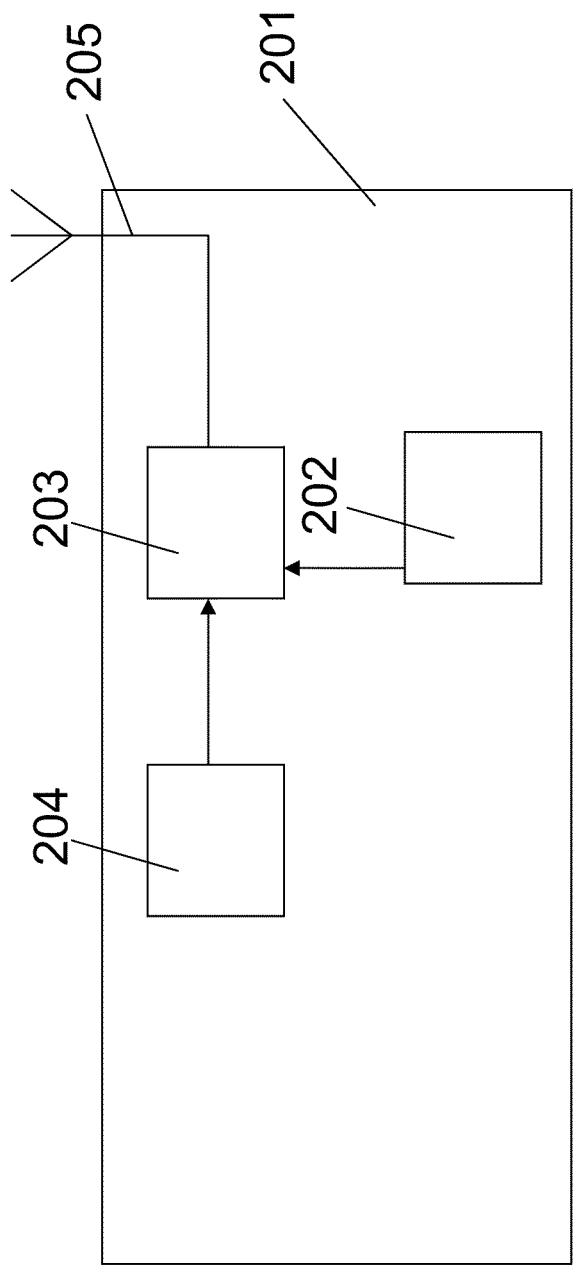
FIG. 2 is a schematic view illustrating an implant according to the invention including selected components.

FIG. 2 is a schematic view illustrating an implant 201 according to the invention including some of the relevant components. Whenever the interference-field detection unit 204 detects an electromagnetic interference, a signal is given to the communications device 203. In one preferred embodiment, the signal is generated only when a predeterminable threshold has been reached or exceeded and/or in response to properties characterizing the interference. After receiving a corresponding signal about a detected interference from interference-field detection unit 204, communications unit 203 transmits a signal through an antenna 205 to the MRI device. In another embodiment, communications unit 203 transmits a signal through antenna 205 not only to an MRI device but to other predeterminable devices that produce electromagnetic interference, such as but not limited to those coming from safety locks, metal detectors, X-ray machines, transmitters, and radar equipment.

Alternatively, communications unit 203 in connection with antenna 205 can also enable a bidirectional link for the purpose of data transfer; specifically in these cases, precise detection of the source of the electromagnetic interference is not absolutely necessary since in this case the source of interference can identify itself to the implant.

Figure 3:
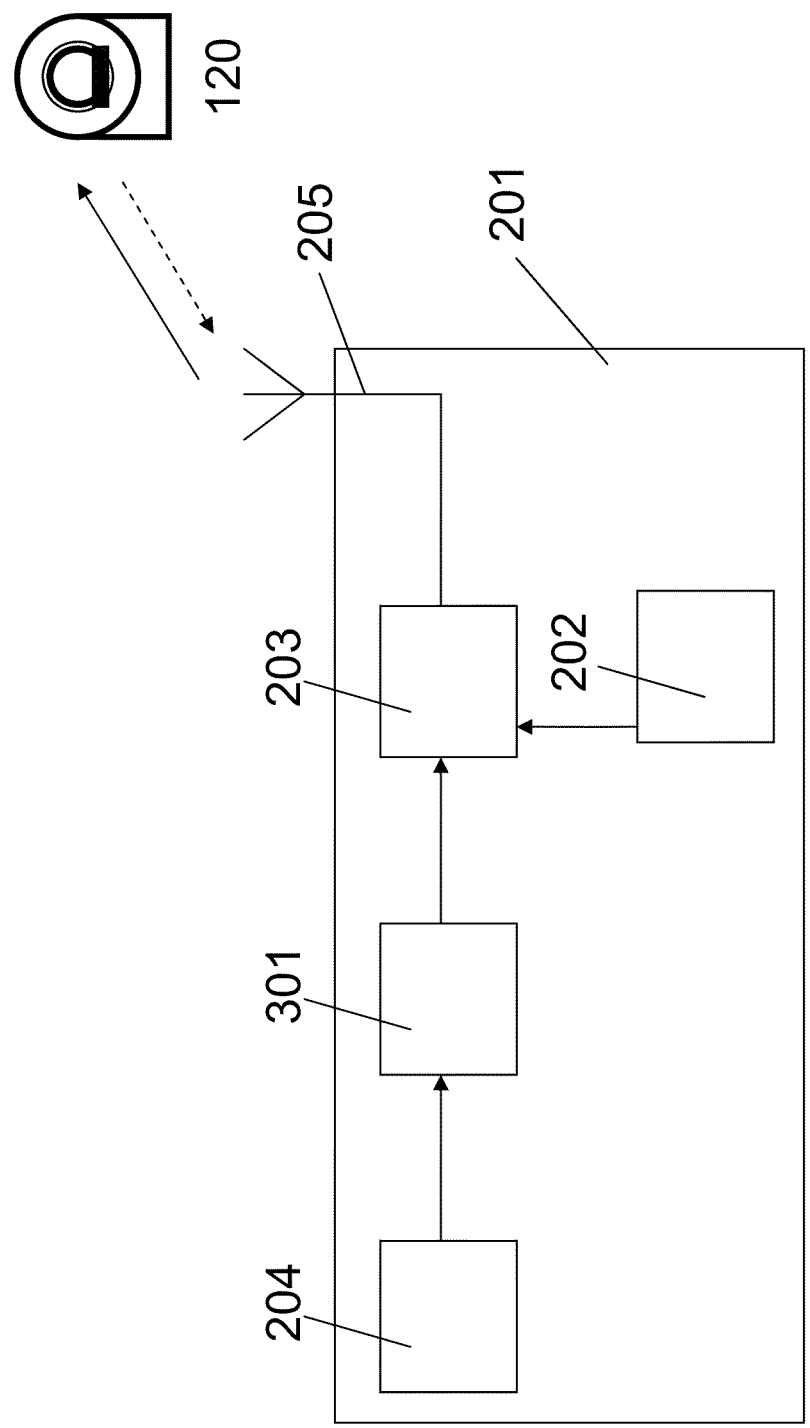
FIG. 3 is a schematic view illustrating an implant according to the invention including selected components in communication with an MRI device.

FIG. 3 illustrates another exemplary embodiment in which the interaction of implant and MRI device or other interference source for electromagnetic interference is shown schematically. Whenever interference-field detection unit 204 detects electromagnetic interference, a signal is transmitted through a delay element 301 to communications device 203. The communications unit then transmits data from memory 202 through antenna 205. Through delay element 301, the signal of the implant hits in the read-out phase or detection phase of the interference source, or of the MRI device, and thus calls attention to the implant through interference of the detection and/or read-out. Alternatively, the signal from the implant can transmit not only an interference, e.g., image interference, to the MRI device, but can also show targeted information on the image generated by the MRI device, e.g., explicit instructions on safely performing the MRI examinations. These instructions can, among other things, relate to maximum allowable intensities, exposure times, or the coordination of implant activity and MRI examination. In the event of an allowable interference, that is, when, for example, the predeterminable threshold values are not reached or exceeded during the MRI examination, the system can also be used to transmit other critical information to the MRI device or the interference source—for example, information about the state of the implant patient, specifically in response to events that produce a worsening of health status and/or a life-threatening state.

As was already pointed out, in one embodiment the interference emanating from the implant can either be capable of being turned off and/or the interference is taken into account or excluded during the MRI examination, and/or the interference is stopped if the predeterminable threshold values are not exceeded and/or reached, and/or characteristics are no longer being met and the interference is thus classified as being compatible with the function of the implant.

Antenna 205 can be either an already present RF antenna and/or a specially dedicated antenna. In particular, electrode leads can also be used as antennas.

In another embodiment, transmission by the signaling system is effected only when the MR sensors in the implant meet a threshold value—in particular, if the scanner has readjusted itself correctly, the threshold value is no longer met.

In another embodiment, the implant carries an RFID that is intended precisely for this purpose of transmitting to the MR scanner the required information, in particular in regard to safety.

Figure 4:
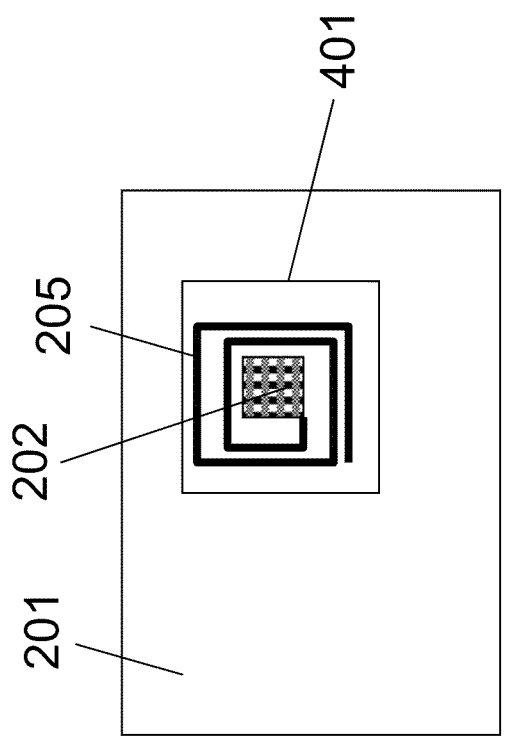
FIG. 4 is a schematic view illustrating a special design of an implant according to the invention.

FIG. 4 illustrates a special solution according to the invention in the form of an implant 201 comprising an RFID tag 401 that is connected to memory 202 and antenna 205. Whenever the implant is exposed to an electromagnetic interference source, e.g., an MRI device, that meets the pre-settable specifications of the RFID tag, RFID tag 401 transmits predeterminable data from the memory 202 containing the safety-relevant information through antenna 205. These data can be interpreted either directly by the interference source or the MRI device, or the data can generate an interference, or alert or any other type of message in the imaging display, wherein the interference itself is capable of reproducing information in the imaging display.

What is preferred in particular with all embodiment variants is that the MRI detection be effected as early as possible and that the control of the MRI device or of another interference source be effected as early as possible. The control here can be provided by an image interference. In this context, early as possible can mean that the signaling or control is effected during a survey scan or the initialization of the MRI device or other interference source.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device comprising:
   a memory configured to hold information;
   at least one antenna and/or at least one telemetry antenna;
   a communications device connectable to the at least one antenna and/or the at least one telemetry antenna,
      wherein said communications device is configured to communicate with a magnetic resonance imaging (MRI) device;
   at least one sensor or indicator configured to detect electromagnetic interference fields;
   a control unit coupled with said memory, said at least one antenna and/or at least one telemetry antenna, said communications device and said at least one sensor or indicator configured to detect electromagnetic interference fields;
   wherein said at least one sensor or indicator is further configured to send a first signal to said control unit;
   wherein the control unit is configured to
      receive said first signal from said at least one sensor or indicator configured to detect electromagnetic interference fields whenever an electromagnetic interference field is detected,
      receive a second signal transmitted from the MRI device through the communications device, and
      control the communications device to emit a third signal through the at least one antenna and/or the at least one telemetry antenna, wherein said third signal is interpretable by the MRI device, wherein the control unit initiates the transmission of the third signal either directly after said control unit receives the first and/or second signal, or after said control unit receives the first and/or the second signal using a time delay;

wherein said transmission is effected through a targeted generation of an image interference with said third signal; and wherein the communications device is configured to provide communication between the magnetic resonance imaging device and the implantable medical device.

2. The implantable medical device according to claim 1, wherein the memory contains data and/or parameters configured to allow a risk-free MRI examination or an MRI examination with reduced risks, compared to an MRI examination performed without said communications device, wherein said data and/or parameters are transmitted to the magnetic resonance imaging device from the communications device with the third signal via the at least one antenna and/or the at least one telemetry antenna whenever an electromagnetic interference field has been detected and/or the communications device has detected a connection to the magnetic resonance imaging device.

3. The implantable medical device according to claim 1, wherein said at least one sensor or indicator configured to detect electromagnetic interference fields is further configured to transmit measured values to the control unit, and the control unit is configured to perform an adjustment of information and/or parameters in accordance with the measured values before the measured values are transmitted from the communications device to the magnetic resonance imaging device, wherein the adjustment is based on values and/or algorithms that are stored in the memory.

4. The implantable medical device according to claim 1, wherein the third signal includes at least one of the following values and/or parameters:
    maximum allowable radio frequency or RF power based on measurement values of the at least one sensor or indicator,
    maximum allowable gradient performance based on measurement values of the at least one sensor or indicator,
    maximum allowable scan duration, as a function of one more of the parameters other than maximum allowable scan duration,
    patient position,
    maximum allowable examination time, and/or
    parameters configured to synchronize magnetic resonance imaging scans and/or magnetic resonance imaging read-out phases and implantable medical device activity relative to signal detection and/or delivery of therapy.

5. The implantable medical device according to claim 1, wherein the implantable medical device is configured to effect an image interference, via signal emission, on a corresponding Larmor frequency during a read-out phase of the MRI device, wherein the signal to effect image interference has a predetermined modulated amplitude.

6. The implantable medical device according to claim 5, wherein the corresponding Larmor frequency is determined by measuring a static magnetic field and/or the frequency of the previous electromagnetic interference via said at least one sensor or indicator configured to detect electromagnetic interference fields.

7. The implantable medical device according to claim 6, wherein a configuration of the signal initiated by the communications device to effect image interference is computed from measurements of the at least one sensor or indicator configured to detect electromagnetic interference fields, and wherein said configuration comprises one or more of a carrier frequency, modulation type, modulation frequency and modulation depth, or any combination thereof.

8. The implantable medical device according to claim 1, wherein maximum allowable performance values for the magnetic resonance imaging device are configured to be transmitted to the magnetic resonance imaging device and adjusted by the control unit based on updated measured values from the at least one sensor or indicator configured to detect electromagnetic interference fields.

9. The implantable medical device according to claim 1, wherein the implantable medical device does not have an internal power supply, or said internal power supply is not available due to the detection of electromagnetic interference, and/or a battery configured to provide communication with the magnetic resonance imaging device is configured to be dispensed with in order to remove a load from the battery, wherein said third signal is transmitted by the communications device and wherein power induced by the magnetic resonance imaging device is configured to power the communications device to transmit said third signal to the magnetic resonance imaging device.

10. The implantable medical device according to claim 1, wherein the at least one antenna and/or at least one telemetry antenna configured to communicate with a magnetic resonance imaging device are composed of elongated subsystems, wherein said elongated subsystems comprise one or more of electrodes of cardiac pacemakers, defibrillators/cardioverters, devices to effect cardiac resynchronization, or neurostimulators, and/or an integrated antenna for radio frequency or RF communication.

11. The implantable medical device according to claim 1, wherein the communication between the magnetic resonance imaging device and the implantable medical device is bidirectional, and wherein the magnetic resonance imaging device transmits, after receipt of parameters that have been transmitted by the communications device of the implantable medical device, an acknowledgement to the implantable medical device, after which the implantable medical device ceases to transmit said third signal or modifies at least the amplitude and/or other parameters of said third signal.

12. The implantable medical device according to claim 1, wherein when electromagnetic interference fields are detected, said control unit is configured to perform at least one of the following:
    switch to a magnetic resonance imaging-safe state,
    remain for an extended time in a magnetic resonance imaging-safe state or a state that is insensitive to electromagnetic interference fields, and
    deliver a therapy and/or detect electrical states in tissue only within time windows in which no electromagnetic interference fields are detected, and/or reconstruct a measurement for those regions in which detection is not permitted due to detection of electromagnetic interference fields.

13. The implantable medical device according to claim 1, wherein the at least one sensor or indicator includes at least one of the following sensors or indicators:
    GMR sensor,
    MagFET sensor,
    Hall sensor,
    electro-optical converter,
    battery voltage sensor configured to monitor voltage during capacitor charging,
    RF field detector,
    magnetic gradient field detector, current detector for currents induced by electromagnetic fields,
vibration detector, for detection of vibrations induced by Lorentz forces.

14. A method comprising:
using an implantable medical device configured to communicate with a magnetic resonance imaging device;
communicating with said implantable medical device, wherein said implantable medical device comprises:
a memory configured to hold information;
at least one antenna and/or at least one telemetry antenna;
a communications device connectable to the at least one antenna and/or the at least one telemetry antenna;
wherein the communications device is configured to provide communication between the magnetic resonance imaging device and the implantable medical device;
at least one sensor or indicator configured to detect electromagnetic interference fields;
a control unit coupled with said memory, said at least one antenna and/or at least one telemetry antenna, said communications device and said unit configured to detect electromagnetic interference fields;
wherein the control unit is configured to
receive a first signal from the unit configured to detect electromagnetic interference fields whenever an electromagnetic interference field is detected,
receive a second signal transmitted from said magnetic resonance imaging device through the communications device, and
control the communications device to emit a third signal through the at least one antenna and/or the at least one telemetry antenna, wherein said third signal is interpretable by the magnetic resonance imaging device, wherein the control unit initiates the transmission of the third signal both directly after said control unit receives the first and/or second signal, or after said control unit receives the first and/or the second signal using a time delay.

15. The method according to claim 14, wherein said transmission is effected through a targeted generation of an image interference with said third signal.

* * * * *